(12) United States Patent
Ono et al.

(10) Patent No.: US 10,151,725 B2
(45) Date of Patent: Dec. 11, 2018

(54) SENSOR SYSTEM AND DEVICE

(71) Applicant: HITACHI AUTOMOTIVE SYSTEMS, LTD, Hitachinaka-shi, Ibaraki (JP)

(72) Inventors: Kazuo Ono, Tokyo (JP); Toshiyuki Usagawa, Tokyo (JP)

(73) Assignee: HITACHI AUTOMOTIVE SYSTEMS, LTD., Ibaraki (JP)

( * ) Notice: Subject to any disclaimer, the term of this patent is extended or adjusted under 35 U.S.C. 154(b) by 0 days.

(21) Appl. No.: 15/541,037

(22) PCT Filed: Dec. 2, 2015

(86) PCT No.: PCT/JP2015/083889
§ 371 (c)(1),
(2) Date: Jun. 30, 2017

(87) PCT Pub. No.: WO2016/111098
PCT Pub. Date: Jul. 14, 2016

(65) Prior Publication Data
US 2017/0370875 A1 Dec. 28, 2017

(30) Foreign Application Priority Data
Jan. 9, 2015 (JP) .................................. 2015-003464

(51) Int. Cl.
*G01N 27/414* (2006.01)
*G01N 27/00* (2006.01)
(Continued)

(52) U.S. Cl.
CPC ........... *G01N 27/4141* (2013.01); *G01K 7/01* (2013.01); *G01N 27/00* (2013.01);
(Continued)

(58) Field of Classification Search
CPC ............ G01N 27/4141; G01N 27/4148; H01L 23/34; G01R 19/10
(Continued)

(56) References Cited

U.S. PATENT DOCUMENTS

| 4,874,499 A | 10/1989 | Smith et al. |
| 2009/0026082 A1* | 1/2009 | Rothberg ............. C12Q 1/6869 204/556 |

(Continued)

FOREIGN PATENT DOCUMENTS

| JP | 63-171351 A | 7/1988 |
| JP | 02-093357 A | 4/1990 |

(Continued)

OTHER PUBLICATIONS

Tsukada, Keiji, et al. "Dual-gate field-effect transistor hydrogen gas sensor with thermal compensation." Japanese Journal of Applied Physics 49.2R (2010): 024206.*

(Continued)

*Primary Examiner* — Fernando L Toledo
*Assistant Examiner* — Adam S Bowen
(74) *Attorney, Agent, or Firm* — Volpe and Koenig, P.C.

(57) ABSTRACT

The invention achieves a lower noise of a sense signal of a FET-type hydrogen sensor. For solving the above problem, one aspect of a sensor system of the invention includes a reference device and a sensor device configured using FETs on a substrate, and further, well potentials of the reference device and the sensor device are electrically isolated from each other.

10 Claims, 15 Drawing Sheets

(51) Int. Cl.
- *G01K 7/01* (2006.01)
- *H01L 21/822* (2006.01)
- *H01L 21/8234* (2006.01)
- *H01L 21/761* (2006.01)
- *H01L 29/78* (2006.01)
- *H01L 27/04* (2006.01)
- *H01L 27/06* (2006.01)
- *H01L 27/08* (2006.01)
- *H01L 27/088* (2006.01)
- *H01L 23/34* (2006.01)
- *G01R 19/10* (2006.01)

(52) U.S. Cl.
CPC ....... *G01N 27/4148* (2013.01); *H01L 21/761* (2013.01); *H01L 21/822* (2013.01); *H01L 21/8234* (2013.01); *H01L 23/34* (2013.01); *H01L 27/04* (2013.01); *H01L 27/06* (2013.01); *H01L 27/08* (2013.01); *H01L 27/088* (2013.01); *H01L 29/78* (2013.01); *G01R 19/10* (2013.01)

(58) Field of Classification Search
USPC .......................................................... 257/253
See application file for complete search history.

(56) References Cited

U.S. PATENT DOCUMENTS

2010/0207206 A1* 8/2010 Krischke ............ H01L 29/0642
257/337

2012/0217550 A1* 8/2012 Usagawa ............ G01N 27/4141
257/253

2013/0186178 A1 7/2013 Usagawa

FOREIGN PATENT DOCUMENTS

| JP | 03-033646 A | | 2/1991 |
| JP | 03033646 A | * | 2/1991 |
| JP | 2012-073154 A | | 4/2012 |
| JP | 2013-064746 A | | 4/2013 |
| WO | 2011/055605 A1 | | 5/2011 |

OTHER PUBLICATIONS

Usagawa, T., et al., "Pt—Ti—O Gate Si-MISFET Hydrogen Gas Sensors—Devices and Packagings," IEEE Sensors Journal, vol. 12, No. 6, Jun. 2012, pp. 2243-2248.

International Search Report, PCT/JP2015/083889, dated Mar. 1, 2016, 3pgs.

Tsukada, K,. et al., "Dual-Gate Field-Effect Transistor Hydrogen Gas Sensor with Thermal Compensation", Japanese Journal of Applied Physics, Feb. 22, 2010, 49 (2010) 024206, 5 pgs.

Japanese Office Action dated Oct. 3, 2017 for the Japanese Patent Application No. 2015-003464.

Japanese Office Action dated Apr. 17, 2018 for the Japanese Patent Application No. 2015-003464.

* cited by examiner

SENSOR SYSTEM AND DEVICE

TECHNICAL FIELD

The present invention relates to a technique for sensing a target with high accuracy when sensing the target based on the difference between outputs of a sensor device and a reference device in a FET-type sensor system.

BACKGROUND ART

A reduction in the emission of $CO_2$, which is a greenhouse effect gas, is a global problem from the viewpoint of global environmental protection. For suppressing the emission from vehicles, the development of a fuel cell vehicle (FCV) using hydrogen as a fuel, which emits only water when burned, has progressed. In the FCV, it is desirable to mount a hydrogen concentration meter for hydrogen concentration control at the time of hydrogen combustion and sensing of hydrogen leakage from piping. Especially, hydrogen is known to explode when the concentration in the air reaches 3.9%; therefore, in the application for sensing of hydrogen leakage, a safety measure such as issuing an alert by the hydrogen concentration meter before the concentration reaches the above explosion limit concentration is desirable. Moreover, since the fuel economy performance can be improved by optimizing the hydrogen concentration at the time of combustion, it is desirable to monitor the hydrogen concentration for the purpose of providing feedback on combustion conditions.

Hydrogen sensors that are in practical use at present include those of a contact combustion type, a semiconductor type, and a gas heat conduction type. In addition to the above, types in the development stage include a solid electrolyte type and a FET type.

The contact combustion type is a type that detects the temperature rise of a catalytic metal such as platinum (Pt) or palladium (Pd) caused by the combustion of hydrogen on the surface of the catalytic metal. The contact combustion type has drawbacks such as having low selectivity while having high hydrogen sensitivity, requiring oxygen for detection, requiring a contrivance for a detection circuit because of a small output, and having large power consumption because the operating temperature is as high as approximately 400° C. and a device needs to be maintained at a high temperature.

The semiconductor type is such that a carrier concentration changes because, due to oxidation reaction of hydrogen on the surface of metal oxide semiconductor, a depletion layer within the semiconductor changes and a change in electrical conduction caused by the change in carrier concentration is detected. The semiconductor type has drawbacks such as requiring oxygen for causing oxidation reaction on the surface of metal oxide semiconductor, and having large power consumption because the operating temperature is as high as approximately 500° C. and a device needs to be maintained at a high temperature.

The gas heat conduction type is such that since a thermal conductivity changes with hydrogen being mixed into an atmosphere gas, hydrogen is detected by detecting the amount of change in the amount of heat released from a device. The gas heat conduction type has the advantage of small power consumption because the operating temperature is relatively as low as approximately 200° C., but is not suitable for use in the application for sensing of hydrogen leakage because it is difficult to detect hydrogen at a low concentration.

Moreover, as to the FET (field-effect transistor) type sensor, an example of having a Pt—Ti—O gate structure is disclosed in Non Patent Literature 1.

CITATION LIST

Patent Literature

Non Patent Literature 1: IEEE Sensors Journal, vol. 12, No. 6, June 2012. "Pt—Ti—O Gate Si-MISFET Hydrogen Gas Sensors-Devices and Packagings"

SUMMARY OF INVENTION

Technical Problem

When a hydrogen sensor that is in practical use is used for sensing of hydrogen leakage in the FCV, the contact combustion type and the semiconductor type, which can detect hydrogen at a low concentration with high accuracy, are candidates. However, we have found by experiment that these types have the drawback of being susceptible to poisoning by cyclic siloxane, which is an environmental material. In contrast to this, the inventors have also confirmed simultaneously by experiment that the FET-type hydrogen sensor having a Pt—Ti—O gate structure has high tolerance to poisoning by cyclic siloxane.

FIG. 1 shows an overview of experimental results. The vertical axis shows the hydrogen concentration in arbitrary units, while the horizontal axis shows the time axis. The graph shows a comparison of measurement results between a FET-type hydrogen sensor (FET-based sensor) and contact combustion type (Catalytic combustion) and oxide semiconductor sensors (Oxide semiconductor sensor). A detailed structure of the FET-type hydrogen sensor having a Pt—Ti—O gate structure used in the experiment is described in detail in Non Patent Literature 1. Cyclic siloxane is released from asphalt used for road pavement, or silicone produces, into an environmental atmosphere, and is known to be a possible cause of faulty electrical continuity at contacts of electrical products at a high temperature.

According to FIG. 1, in the case of performing measurements at a hydrogen concentration of, for example, approximately 0.5, since activity against hydrogen is lost at approximately 100 seconds in a cyclic siloxane atmosphere and sensitivity decreases in the contact combustion type and the semiconductor type, a hydrogen concentration to be detected decreases. On the other hand, since catalytic activity does not almost change in the FET-type hydrogen sensor, a hydrogen concentration to be detected does not change.

Since the contact combustion type and the semiconductor type operate at a high temperature of 400° C. or more, cyclic siloxane is oxidized at the surface of a catalyst. As a result of this, a mechanism is considered, in which silicon oxide adheres to the surface and covers the active site of the catalyst for hydrogen, and catalytic action on hydrogen is lost. In the FET-type hydrogen sensor, it is considered that such a phenomenon does not occur because the operating temperature is relatively as low as approximately 100° C. and thus activity is maintained. It can be said that the FET-type hydrogen sensor is a hydrogen sensor that can be applied to the FCV because tolerance to cyclic siloxane is high. The invention of the present application relates to this FET-type hydrogen sensor.

According to FIG. 2, a hydrogen sensing mechanism of the FET-type hydrogen sensor concerned by the invention of the present application will be described.

FIG. 2A shows an overview of a device cross-section of a reference FET, and FIG. 2B shows an overview of a device cross-section of a sensor FET. The device cross-sectional structures of the reference FET and the sensor FET are manufactured to be substantially the same, including the size and a film configuration. The reference FET and the sensor FET are formed on the same silicon substrate (SUB). That is, in FIG. 2, the reference FET and the sensor FET are separately described in FIGS. 2A and 2B; actually, however, the respective substrates (SUB) are connected, so that the reference FET and the sensor FET are formed adjacent to each other on the same substrate (SUB). A well (WELL) is provided on the substrate (SUB), and a FET device is formed in the well (WELL).

Although there are various kinds of catalytic gate electrodes (CATGATE) such as a stacked film of Pt—Ti—O and a Pd film, all catalytic gates having activity against hydrogen gas are concerned in the FET-type hydrogen sensor in the present application. A gate insulating film (OXIDE) is configured of $SiO_2$ in most cases, similarly to a common FET. However, the FET-type hydrogen sensor of the present application is not limited to this. In the reference FET, the catalytic gate electrode (CATGATE) is covered by a detection target blocking film (PASSI). Since the detection target blocking film (PASSI) does not have hydrogen permeability, hydrogen does not reach the catalytic gate electrode (CATGATE); therefore, the reference FET does not have hydrogen sensitivity while having the same structure as the sensor FET.

Although not shown in FIG. 2, the sensor FET is configured such that, by providing a through hole or the like in a protective film or the like covering the catalytic gate electrode (CATGATE), the catalytic gate electrode (CATGATE) is exposed to hydrogen.

Bias conditions of the sensor FET and the reference FET will be described. The same drain-source voltage (VDS) is applied to drain and source terminals of each of the sensor FET and the reference FET. The drain terminal of the reference FET is shown by (DREF), the source terminal thereof is shown by (SREF), the drain terminal of the sensor FET is shown by (DSEN), and the source terminal thereof is shown by (SSEN). Further, the same gate voltage (VG) is applied to gates of the sensor FET and the reference FET. The gate voltage (VG) is a gate potential based on the groundpotential, and is not a gate potential with respect to a source potential. A well potential (BREF) and the source terminal (SREF) of the reference FET are connected, and a well potential (BSEN) and the source terminal (SSEN) of the sensor FET are connected, to cause operation. Due to this, the substrate effect, in which the threshold voltage of the FET varies due to the voltage of the substrate, can be removed. (VREF) is the output of the reference FET, and (VSEN) is the output of the sensor FET.

As shown in FIG. 2B, hydrogen gas is decomposed into hydrogen atoms or hydrogen ions by the catalytic action of the catalytic gate electrode (CATGATE) of the reference FET. This decomposed hydrogen is occluded by the catalytic gate electrode (CATGATE) and forms a dipole (DIPOLE) in the vicinity of the interface between the gate insulating film (OXIDE) and the catalytic gate electrode (CATGATE). By the action of this dipole (DIPOLE), a threshold voltage change of $\Delta V$ is generated in the sensor FET, compared to the reference FET, and the hydrogen concentration is determined by detecting the threshold voltage change by a detection circuit.

FIG. 2C is a schematic diagram of a comparison of IDS-VDS characteristics between the reference FET and the sensor FET at the time of sensing hydrogen. Since the same current (IDS) that flows from the drain to the source is applied, an operating current is the same. Moreover, since the same drain-source voltage (VDS) is applied, the IDS-VGS curves have the same shape for the reference FET (shown by the dotted line) and the sensor FET (shown by the solid line) but the curve for the sensor FET has the shape of being shifted by $\Delta V$ to the negative side of VGS. In this manner, the threshold voltage change $\Delta V$ appears as the difference between a gate-source voltage Vgs0 in the reference FET and a gate-source voltage Vgs in the sensor FET. Since VG is the same in the reference FET and the sensor FET as described above, $\Delta V$ is finally detected as the difference between the source potentials of the reference FET and the sensor FET due to Vgs=VG−VS.

In addition to an operating method in which the difference $\Delta V$ in voltage is detected with the current being constant as in the above, operating methods include an operating method in which a difference $\Delta I$ in current is detected with the voltage being constant. In the device of FIG. 2, the value of $\Delta V$ can be taken large, and moreover, a correlation with the hydrogen concentration is strong; therefore, there is a merit in detecting a voltage difference.

In the previous description, an example in which a sensing target gas is hydrogen has been described. However, sensing of various gases other than hydrogen is possible by changing the kind of the catalytic metal CATGATE in the FET-type sensor, and therefore, the overall problem of a FET-type gas sensor will be described in the following description.

The problem will be described with FIG. 3 showing an overview of a cross-sectional structure of a conventional FET-type gas sensor. Two independent P-wells (PWELL) are provided on a P-type substrate (PSUB), and one N-channel FET device is formed in each of the P-wells (PWELL). One of the N-channel FET devices is a sensor FET (NCHSENSOR), and the other is a reference FET (NCHREFERENCE). A catalytic metal (CATGATE), a sensing target blocking film (PASSI), and a gate insulating film (OXIDE) are the same as those of FIG. 2. A P-diffusion region (P+) and an N-diffusion region (N+) are each a diffusion layer region where an impurity is implanted at a high concentration for obtaining a contact.

Similarly to FIG. 2, the respective terminals of the sensor FET are shown as a well potential (BSEN), a drain terminal (DSEN), a gate terminal (GSEN), and a source terminal (SSEN). The respective terminals of the reference FET are shown as a well potential (BREF), a drain terminal (DREF), a gate terminal (GREF), and a source terminal (SREF). The feeding potential of the substrate is shown by (SUB). These symbols are used in common in the description.

As seen from FIG. 3, since the P-wells (PWELL) are made adjacent to each other on the same P-type substrate (PSUB), the wells of the reference FET and the sensor FET are electrically connected with a low resistance. For this reason, it is impossible to short-circuit the well and the source as shown in FIGS. 2A and 2B. When hydrogen is sensed in such a state based on the difference in output between the reference FET and the sensor FET, the substrate effect cannot be removed as described below, and it becomes difficult to calculate the concentration of a sensing target.

FIG. 4 shows one example of a sensing system including a circuit that detects an output signal of the sensor device described in FIG. 3. A portion where the well potentials are short-circuited through the substrate is shown by the thick line. As shown in the drawing, the substrate potential is common to the sensor FET and the reference FET. Two independent VTH sensing circuits (VTHSENSE) are analog circuit blocks that amplify and extract the outputs of the reference FET and the sensor FET.

The VTH sensing circuit (VTHSENSE) supplies a drain potential (VDSEN) to the drain terminal (DSEN) of the sensor FET, amplifies a potential (VSSEN) of the source terminal (SSEN), and outputs the potential as the sensor output (VSEN) to an operation circuit (CAL) that performs a correction operation.

Similarly to the VTH sensing circuit (VTHSENSE) connected to the sensor FET, the VTH sensing circuit (VTHSENSE) connected to the reference FET also has the function of supplying a drain potential (VDREF) to the drain terminal (DREF) of the reference FET, amplifying a potential (VSREF) of the source terminal (SREF), and outputting the potential as the sensor output (VREF) to the operation circuit (CAL) performing a correction operation.

The reference FET output and the reference FET output, which are detected by the two VTH sensing circuits (VTHSENSE), are input to the operation circuit (CAL), and the difference between the two sensor outputs (VSEN) and (VREF) is obtained and sent as concentration information of a sensing target (SIG) to a system (SYSTEM).

A reference voltage generating circuit (VGEN) generates a drain-source voltage (VDSSEN) for sensor FET, a drain-source voltage (VDSREF) for reference FET, and the gate voltage (VG) common to the reference FET and the sensor FET.

In the sensor system configured in FIGS. 3 and 4, a threshold voltage Vth_sens of the reference FET and a threshold voltage Vth_ref of the sensor FET are described by Equations (1) below.

$$\text{Vth\_sens} = Vth0 + \frac{1}{Cox}\sqrt{2\varepsilon qN_A(2\phi_F + VG - \text{Vth\_sens})} + \text{Vth\_sen}(1/f) + \Delta V$$

$$\text{Vth\_ref} = Vth0 + \frac{1}{Cox}\sqrt{2\varepsilon qN_A(2\phi_F + VG - \text{Vth\_ref})} + \text{Vth\_ref}(1/f)$$

[Math. 1]

In the equations, Vth0 is a threshold voltage including a noise component included in common in the reference FET and the sensor FET, such as a process variation. Cox is the gate capacitance, $\varepsilon$ is the permittivity, q is the elementary charge, NA is the doping concentration, $\phi F$ is the Fermi energy, and VG is the gate potential, which are common to the reference FET and the sensor FET. Vth_sen (1/f) is a 1/f noise component that is superimposed on the sensor FET output, and Vth_ref (1/f) is a 1/f noise component that is superimposed on the reference FET output. $\Delta V$ is the change in the threshold voltage of the sensor FET due to sensing of a target gas, and this term is not included in the reference FET because the target gas does not contact the catalytic gate electrode (CATGATE) of the reference FET due to the sensing target blocking film (PASSI) of FIG. 3.

It is desirable that only $\Delta V$ is left from the difference between the two equations. However, the second term and the third term on the right side cannot be removed by the difference. This is left as an error at the time of gas detection and degrades measurement accuracy or reliability of the entire sensor system. The second term on the right side is the substrate effect and is a term that appears because a difference is generated between the potentials of the well and the source of each of the reference FET and the sensor FET. The third term on the right side is the term of the 1/f noise well known as the noise of a FET, and this cannot be removed because it is a random noise.

Solution to Problem

For solving the above problem, one aspect of a sensor system of the invention includes a reference device and a sensor device configured using FETs on a substrate, and further, well potentials of the reference device and the sensor device are electrically isolated from each other.

Another aspect of the invention is directed to a system including: a P-type semiconductor substrate; a sensor FET that is formed of a P-type FET within a first N-well formed on the P-type semiconductor substrate and has sensitivity to a sensing target; and a reference FET that is formed of a P-type FET within a second N-well formed on the P-type semiconductor substrate and does not have sensitivity to the sensing target. The first N-well and the second N-well are electrically isolated from each other, and this system includes a detection circuit that detects a difference between threshold voltages of the sensor FET and the reference FET in a gas atmosphere.

Another aspect of the invention is directed to a system including: a semiconductor substrate; a sensor FET that is formed of a FET within a first well formed on the semiconductor substrate and has sensitivity to a sensing target; and a reference FET that is formed of a FET within a second well formed on the semiconductor substrate and does not have sensitivity to the sensing target. The first well and the second well are provided electrically isolated from each other, a source of the sensor FET and the first well are short-circuited, a source of the reference FET and the second well are short-circuited, and the system includes a detection circuit that detects a difference between threshold voltages of the sensor FET and the reference FET in a gas atmosphere.

Further another aspect of the invention is directed to a device including: on the same semiconductor substrate, a semiconductor region; a sensor FET that is formed of a FET within a first well formed in the semiconductor region and has sensitivity to a sensing target; and a reference FET that is formed of a FET within a second well formed in the semiconductor region and does not have sensitivity to the sensing target. This device includes a configuration that prevents electrical continuity between the first well and the second well. Moreover, this device includes a sensor signal output terminal that outputs a signal representing a threshold voltage of the sensor FET or a change in the threshold voltage, and a reference signal output terminal that outputs a signal representing a threshold voltage of the reference FET or a change in the threshold voltage. The output terminal includes one that outputs the signal to the outside of this device, and one that outputs the signal to other circuits within this device.

As one preferred example of the configuration preventing the electrical continuity, an example can be mentioned in which the semiconductor region is a semiconductor region of a first conductivity type, the first and second wells are wells of a second conductivity type, and the electrical continuity between the first and second wells of the second conductivity type is prevented by separating the first and second wells of the second conductivity type by the semiconductor region of the first conductivity type.

Moreover, as another example of the configuration preventing the electrical continuity, an example can be mentioned in which the electrical continuity between the first and second wells of the second conductivity type is prevented by providing a trench-type device isolation structure between the first and second wells.

A structure that generates a signal corresponding to temperature may be provided on the semiconductor substrate, and the structure may be used for various controls or corrections to perform a precise measurement.

Moreover, as a preferred configuration example, a configuration can be mentioned in which the well potential and the source potential of the sensor FET are short-circuited and the well potential and the source potential of the reference FET are short-circuited. Moreover, a configuration may be employed in which the source potential of the sensor FET, which is short-circuited with the well potential, is output to the sensor signal output terminal and the source potential of the reference FET, which is short-circuited with the well potential, is output to the reference signal output terminal.

Advantageous Effects of Invention

A lower noise of a sense signal of a FET-type sensor can be achieved. Problems, configurations, and advantageous effects other than those described above will be apparent from the following description of embodiments.

DESCRIPTION OF EMBODIMENTS

EXAMPLES

Figure 1:
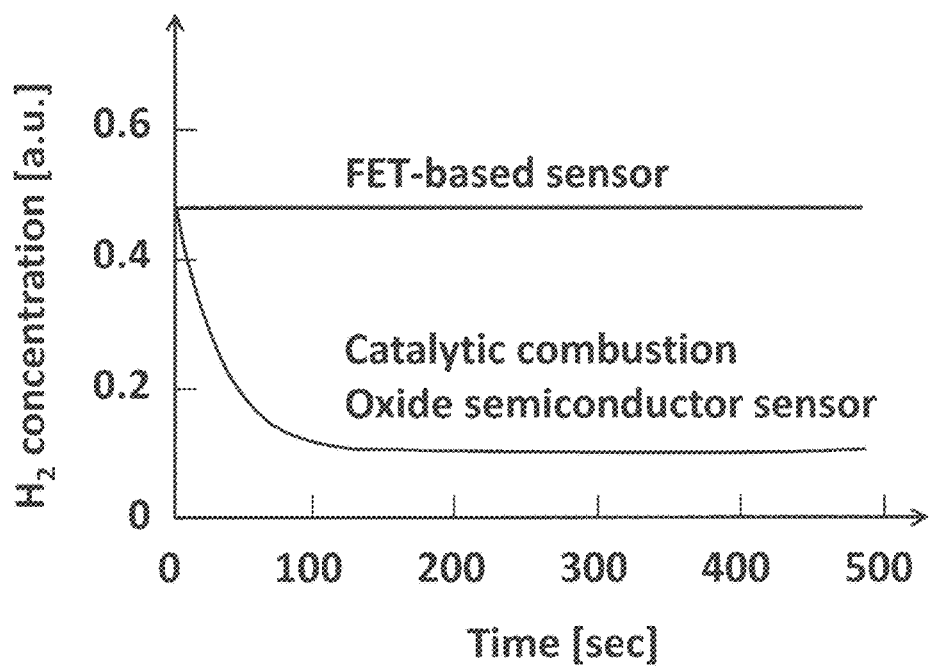
FIG. 1 A graphical representation of tolerance comparison data of hydrogen sensors to cyclic siloxane.

Hereinafter, embodiments of the invention will be described in detail based on the drawings. However, the invention should not be interpreted as being limited to the details described in the embodiments shown below. Those skilled in the art will readily understand that the specific configuration may be modified within the scope not departing from the idea or spirit of the invention. In all of the drawings for describing the embodiments, the same members are denoted in principle by the same reference numerals and signs, and a repetitive description thereof may be omitted.

The terms "first", "second", "third", and the like in the description and the like are used to differentiate components from one another and do not necessarily limit the number or order of the components. Moreover, the numbers for differentiating the component are used for each context, and the number used in one context does not necessarily represent the same configuration in another context. Moreover, a component differentiated by a certain number is not prevented from serving also the function of a component differentiated by another number.

The position, size, shape, range, and the like of each configuration shown in the drawings and the like may not represent actual position, size, shape, range, and the like for facilitating the understanding of the invention. For this reason, the invention is not necessarily limited to the position, size, shape, range, and the like disclosed in the drawings and the like.

A component expressed in a singular form includes components in a plural form unless otherwise specified in a context.

Figure 5:
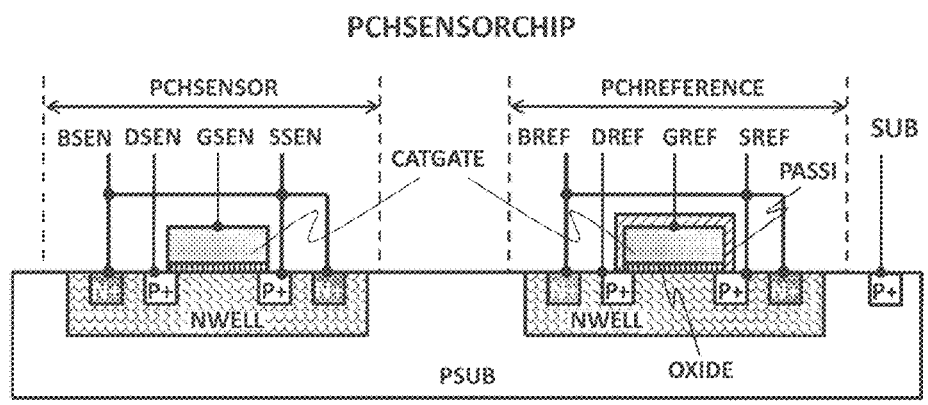
FIG. 5 A cross-sectional view of a P-channel FET-type hydrogen sensor device.

A cross-sectional view of a sensor chip shown in FIG. 5 shows a first example of the present application. A sensor FET (PCHSENSOR) formed of a P-channel FET on a P-type substrate (PSUB) and a reference FET (PCHREFERENCE) also formed of a P-channel FET are formed adjacent to each other. By forming the reference FET and the sensor FET having the same structure adjacent to each other, a manufacturing variation typified by lithography or an implantation concentration can be suppressed, and it is possible to reduce errors when obtaining the difference.

Figure 3:
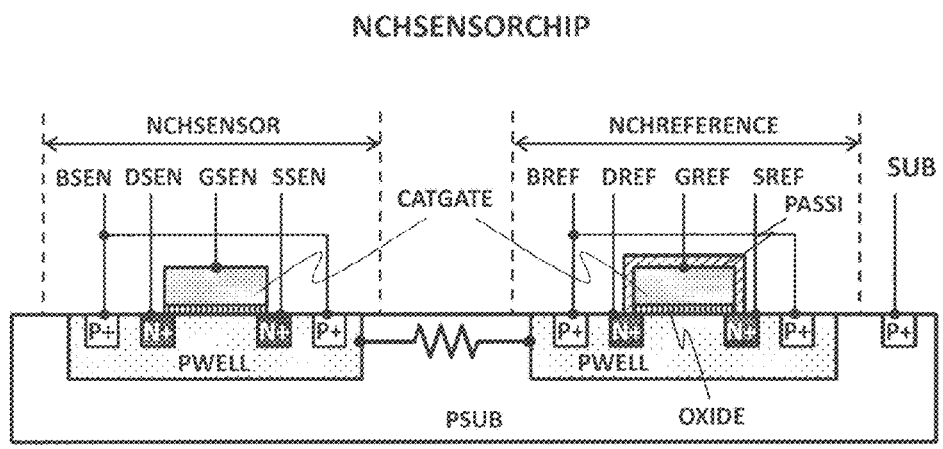
FIG. 3 A cross-sectional view showing a problem of a conventional N-channel FET-type hydrogen sensor device.

The first example is the same as the conventional configuration shown in FIG. 3 in that both the reference FET and the sensor FET include a catalytic gate (CATGATE) and that only the reference FET includes a blocking film (PASSI) to eliminate hydrogen sensitivity. The blocking film (PASSI) may be any film as long as it does not transmit a detection target, such as a stable oxide, for example silicon nitride or silicon oxide, or various kinds of organic films. That is, compared to the conventional configuration, the first example of the present application is different in that the sensor FET and the reference FET are configured of, not N-channel FETs, but P-channel FETs while using the same P-type substrate (PSUB).

N-wells (NWELL) where the respective P-channel FETs are formed are provided independently of each other. As a result of this, the two NWELLs are reversely biased when a feeding potential (SUB) of the P-type substrate (PSUB) is the ground potential, and therefore can be electrically isolated from each other.

For this reason, the N-well (NWELL) potential of the sensor FET and the potential of the N-well (NWELL) of the reference FET can be controlled independently. As a result, as shown in FIG. 5, a well terminal (BSEN) and a source terminal (SSEN) can be short-circuited in the sensor FET, and a well terminal (BREF) and a source terminal (SREF) can be short-circuited in the reference FET.

Figure 6:
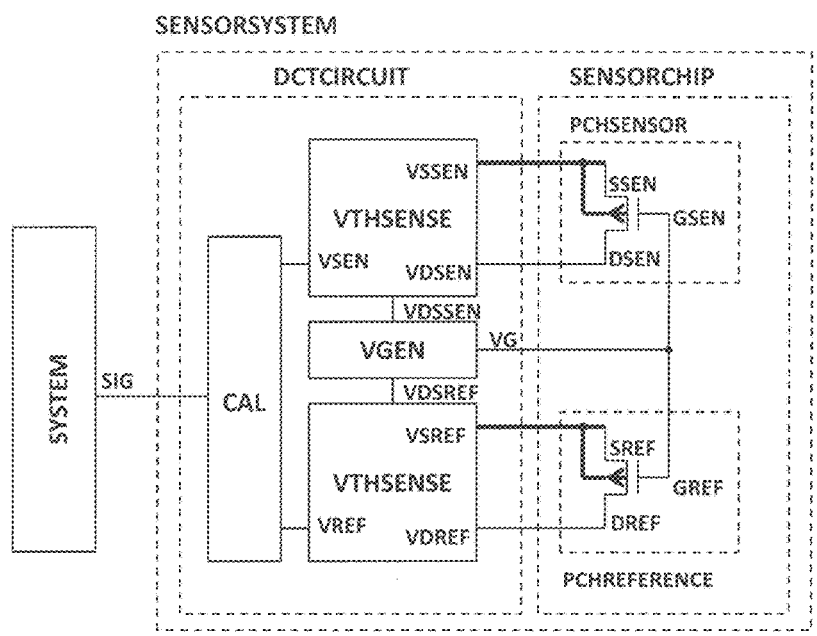
FIG. 6 A schematic view of a P-channel FET-type hydrogen sensor system.

FIG. 6 shows one example of a sensor system using the sensor chip (SENSORCHIP) shown in FIG. 5. In this example, a sensor system (SENSORSYSTEM) is configured using the sensor chip (SENSORCHIP) and a detection circuit (DCTCIRCUIT) as different chips, and this sensor system is further connected to a higher level system (SYSTEM). However, the sensor chip and the detection circuit may be combined into one chip, and further, the higher level system may be included to be combined into one chip.

Figure 4:
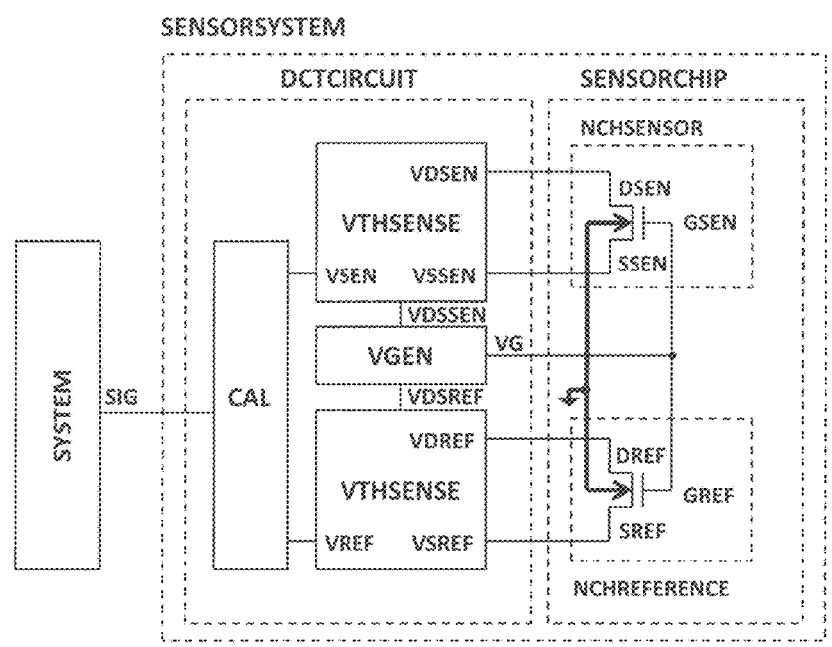
FIG. 4 A schematic view showing a problem of a conventional N-channel FET-type hydrogen sensor system.

Operations of VTH detection circuits (VTHSEN), a reference voltage generating circuit (VGEN), and a correction operation circuit (CAL) are equivalent to those in the description of FIG. 4. However, the N-channel FET is used in FIG. 4, whereas the P-channel FET is used in FIG. 6; therefore, the source and the drain are interchanged. The sensor chip (SENSORCHIP) of FIG. 6 is different from the conventional example shown in FIG. 3 in that the well potential and the source potential are short-circuited in each of the P-channel sensor FET (PCHSENSOR) and the P-channel reference FET (PCHREFERENCE). Due to this, in the sensor system shown in FIG. 6, a threshold voltage Vth_sens of the reference FET and a threshold voltage Vth_ref of the sensor FET are described by Equations (2) below.

$$Vth\_sens = Vth0 + \alpha \cdot Vth\_sen(1/f) + \Delta V$$

$$Vth\_ref = Vth0 + \alpha \cdot Vth\_ref(1/f) \qquad \text{[Math. 2]}$$

Compared to Equations (1), Equations (2) are different in that the term of the substrate effect is absent and further that each of the 1/f noise components becomes small ($\alpha < 1$). The 1/f noise is known to be small in a P-channel FET, compared to an N-channel FET, and $\alpha$ in the third term on the right side can be expected to be approximately 0.5. For this reason, compared to the conventional configuration, the term of the substrate effect is zero and the 1/f noise component is reduced almost by half in the first example of the present application; therefore, a sensing target can be detected with high accuracy. Moreover, when FIG. 3 and FIG. 5 are compared to each other, there is little change in the cross-sectional structure; therefore, there is little difference in ease of manufacturability. That is, higher accuracy of the sensor system becomes possible without increasing manufacturing costs.

When a FET is used as a common electronic device, it is desirable to make the gate width large for obtaining a sufficient current because a P-channel FET has a small ON-current compared to an N-channel FET. That is, since the device size needs to be made large and the chip area becomes large, there is a concern that costs increase. However, when a FET is used as the sensor system shown in FIG. 6, which senses a target based on the difference between the threshold voltages of the reference FET and the sensor FET, a large drain current is not required. Therefore, the drawback of the P-channel FET incapable of taking a large ON-current does not become a problem.

Figure 7A:
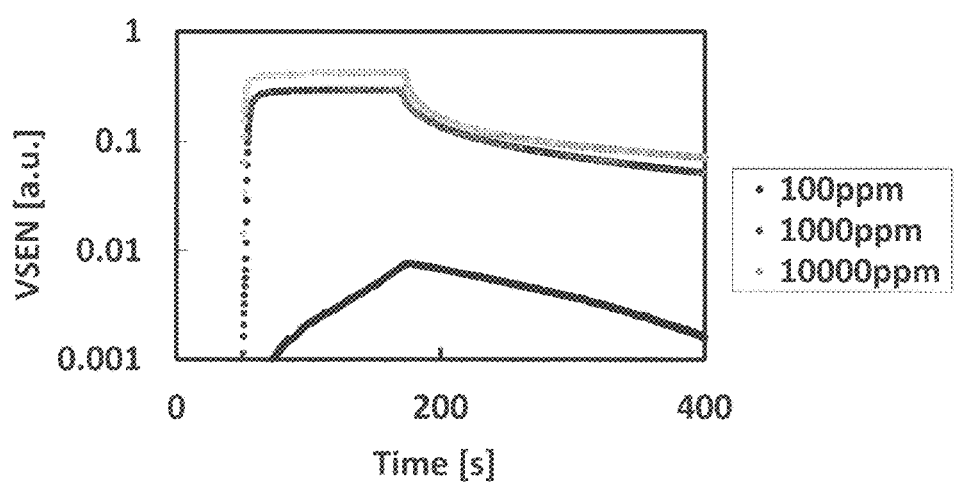
FIG. 7A A graphical representation showing a hydrogen response example of a P-channel FET-type hydrogen sensor.
Figure 7B:
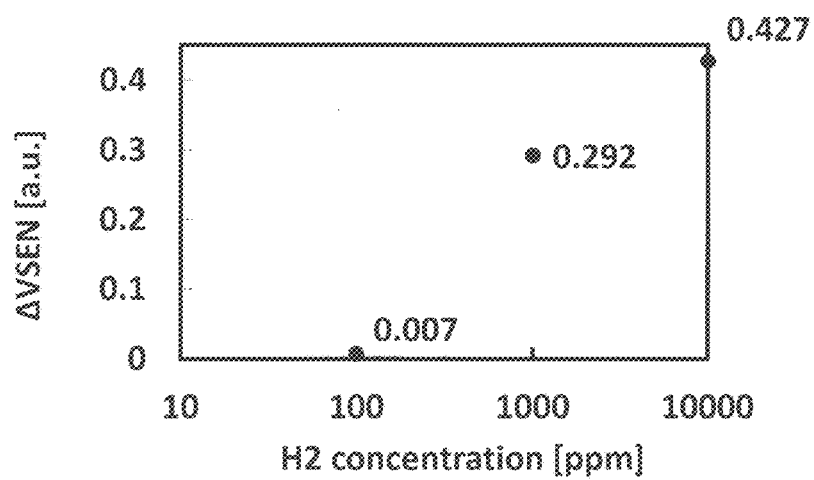
FIG. 7B A graphical representation showing an output characteristics example of the P-channel FET-type hydrogen sensor.

FIG. 7 show output characteristics of a sensor FET formed of an actual P-channel FET. FIG. 7A shows hydrogen response characteristics of a sensor output VSEN. The vertical axis is the output (arbitrary unit) of the FET, while the horizontal axis is the time axis. It is seen that the introduction of hydrogen starts at the timing near several tens of seconds and, at the same time, the output rises. Moreover, the hydrogen introduction stops near 180 seconds, and, at the same time, the output is lowered. FIG. 7B shows the relationship between VSEN and the hydrogen concentration. A favorable hydrogen response was confirmed at concentrations from 100 ppm to 10000 ppm, and it is found that the P-channel sensor FET has almost the same performance as the N-channel sensor FET.

The influence of the substrate effect on threshold voltage sensing will be quantitatively described using FIG. 8.

Figure 2A:
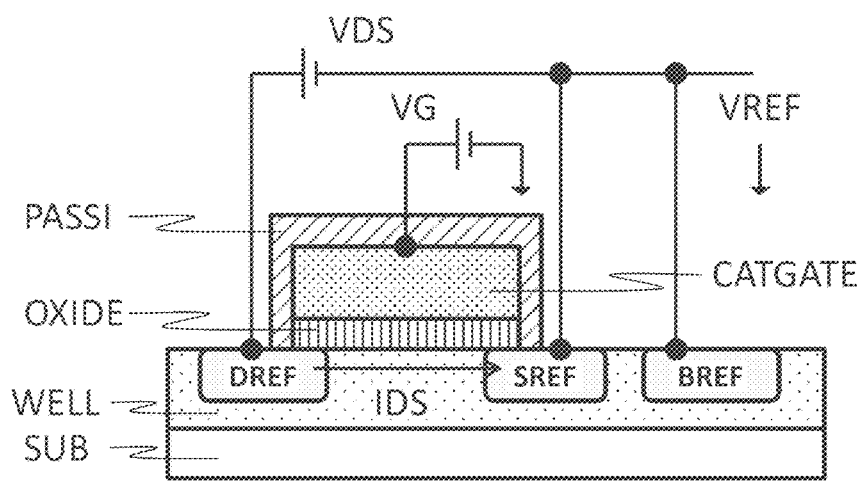
FIG. 2A A cross-sectional view of a reference FET.
Figure 2B:
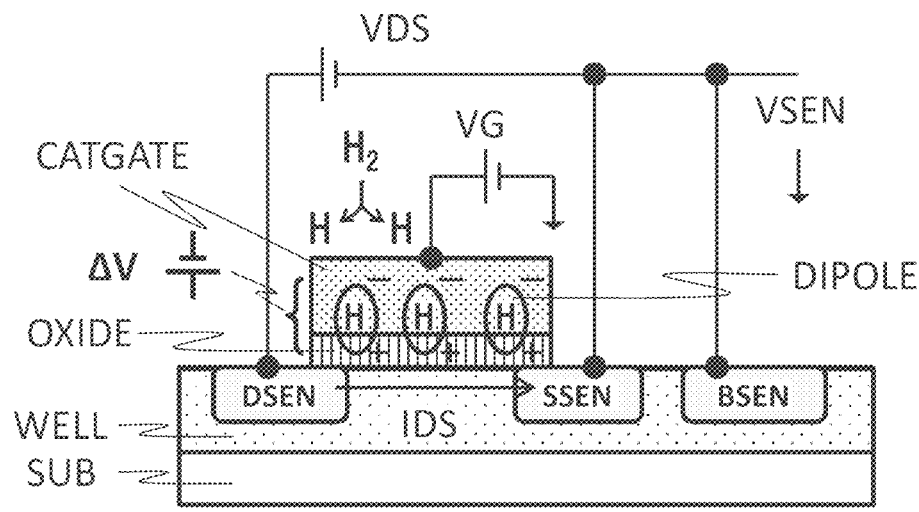
FIG. 2B A cross-sectional view of a sensor FET.
Figure 2C:
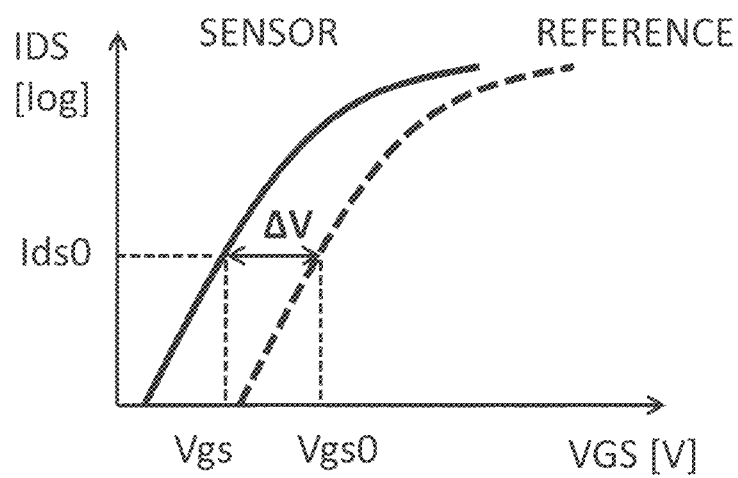
FIG. 2C A graphical representation showing electrical characteristics of a FET-type hydrogen sensor.
Figure 8A:
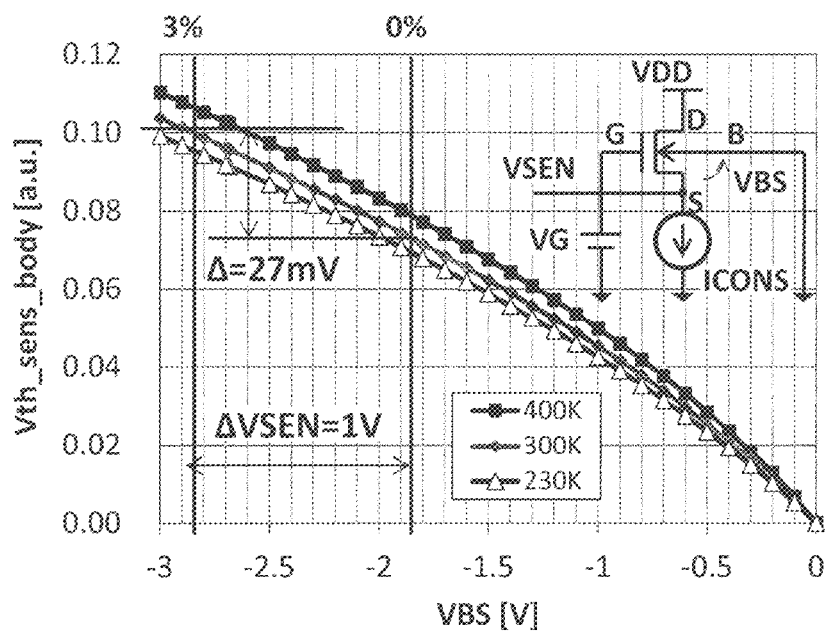
FIG. 8A A graphical representation showing an example of the substrate effect.

FIG. 8A shows the relationship between a substrate voltage VBS and a component Vth_sens_body due to the substrate effect in a threshold voltage change in the sensor FET. The calculation was performed for the case in which an N-channel FET was used and the well potential was grounded without short-circuiting the well and the source. A simplified circuit diagram is as shown in the inset of FIG. 8A, where G is a gate, D is a drain, and S is a source. A constant current source (ICONS) is inserted between the source and the ground potential to realize a constant drain current as shown in FIG. 2C. (VDD) is a power source potential, and (VG) is a gate potential. Moreover, (VSEN) is a sensor output. The calculation was performed at temperatures of 230K, 300K, and 400K. These respectively correspond to −40° C., a room temperature, and approximately 130° C., and cover an operating temperature range required for vehicle applications.

Since the potentials of the source and the well are different from each other, the sensor output (VSEN) and Vth_sens_body increase with an increase in the constant current source (ICONS). VBS is approximately −1.85 V when the constant current source (ICONS) is set to a magnitude required for sensing, and the sensor output (VSEN) is approximately 1.85 V because the well is grounded. This state is defined as a state when a sensing target is at 0%. When the sensing target is present at 3%, the sensor output is 1.0 V, which means that VBS is −2.85V. In the reference FET, since the output does not change even if the sensing target is present, VBS remains at −1.85 V. Therefore, a difference of 1.0 V occurs in VBS between the sensor FET and the reference FET. Due to this, a difference Δ occurring between the threshold voltage of the sensor FET and the threshold voltage of the reference FET is 27 mV. Since an error of 27 mV occurs with respect to the 3% sensing target, a measurement error of 2.7% occurs.

Figure 8B:
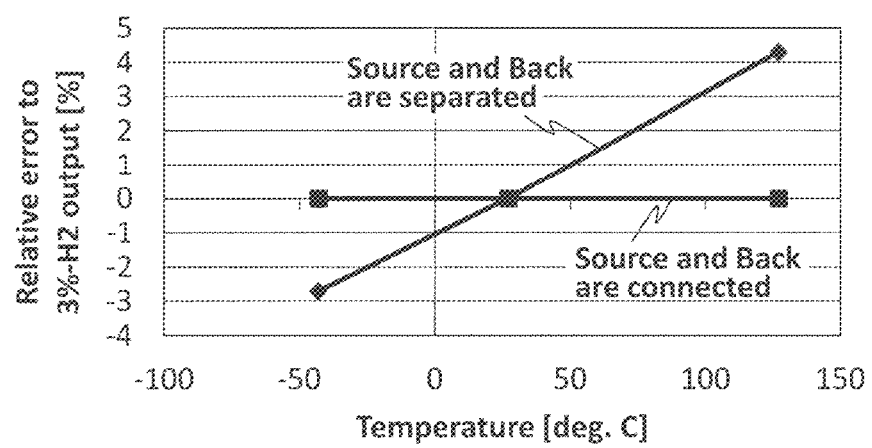
FIG. 8B A graphical representation showing the effect of eliminating the substrate effect.

FIG. 8B was obtained by plotting concentration detection relative errors of the detection target due to the substrate effect shown in FIG. 8A against the temperature. Normalization was performed with relative errors at a room temperature. It is meant that when the detection target is present at a concentration of 3%, a relative error of −3% is superimposed due to the substrate effect in sensing the 3% detection target at −40° C. On the other hand, a relative error of +4% is superimposed due to the substrate effect in sensing the 3% detection target at 130° C. It should be noted that since there is a temperature dependence in the error to be superimposed due to the substrate effect as described above, temperature calibration is required, to correct this, as an adjustment before the shipment of the sensor. This may be a factor in the increase of sensor costs. A Vth variation Vth_body due to the above substrate effect is described as Equations (3) below.

$$\text{Vth\_body} = \gamma\left(\sqrt{\phi_F - VBS} - \sqrt{\phi_F}\right) \quad \text{[Math. 3]}$$

$$\phi_F = 2\frac{k_B T}{q}\ln\left(\frac{N_A}{N_i}\right)$$

$$\gamma = \frac{\sqrt{2\varepsilon q N_A}}{C_{ox}}$$

In the equations, kb is the Boltzmann constant, T is the temperature, and Ni is the intrinsic carrier density. Since the impurity density NA has a temperature dependence, the Vth_body changes depending on the temperature.

In the example of the present application shown in FIGS. 5 and 6, Vth_sens_body=0 V because VBS=0 V, so that the relative error described above does not essentially occur. Therefore, the relative error depending on the temperature is zero as shown in FIG. 8B, extra time and effort for the adjustment can be saved, and an inexpensive and highly accurate sensor can be provided. The advantage due to the removal of the substrate effect by the example of the present application has been described so far. Next, the effect of reducing the 1/f noise will be described using FIG. 9.

Figure 9:
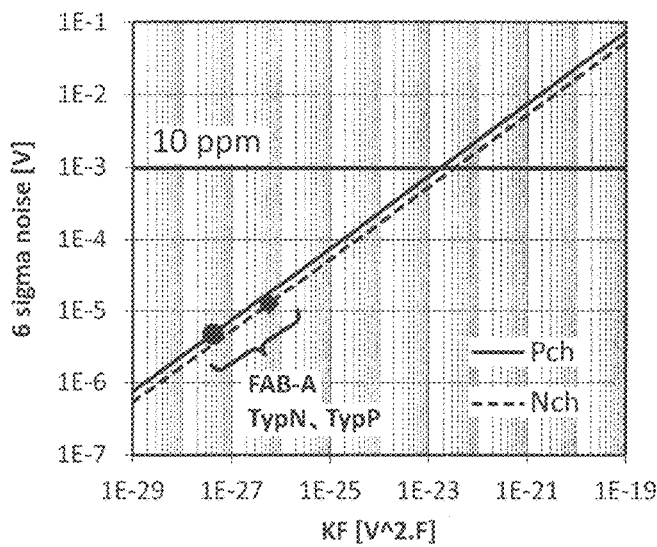
FIG. 9 A graphical representation showing an example of the effect of reducing the 1/f noise.

FIG. 9 shows a comparison of the 1/f noises, calculated using a standard N-channel FET model TypN and a standard P-channel FET model TypP provided in a certain semiconductor manufacturing process FAB-A, between a P-channel FET and an N-channel FET. For calculation, Equation (4) below, which is the 1/f noise calculation equation in BSIM3, was used.

$$\frac{v_n^2}{\Delta f} = \frac{KF}{C_{ox}LWf} \quad \text{[Math. 4]}$$

In the equation, vn is the gate input-referred noise, Δf is the band width, KF is the 1/f noise parameter, L is the gate length of the FET, W is the gate width of the FET, and f is the measured frequency. When the 6sigma noise is calculated, the noise level in FAB-A is low by approximately two orders of magnitude in both the N-channel and the P-channel, compared to the output, when the detection target is present at 10 ppm. However, when a production line in which KF>1E-23 is used, the magnitude of the 1/f noise is approximately the same as the signal output of the detection target 10 ppm and is a non-negligible magnitude.

In this case, since the 1/f noise in the P-channel FET has a magnitude equal to or less than ½ that of the N-channel FET, the P-channel type is advantageous for achieving higher accuracy compared to the N-channel type. The 1/f noise is a random noise as described above and therefore cannot be removed by the difference between the reference FET and the sensor FET. Therefore, it is desirable to make the 1/f noise as low as possible at a sensor chip level. Moreover, the 1/f noise increases as the measurement time is longer; therefore, it is also possible to improve stability or reliability for long-term operation by configuring the sensor FET and the reference FET using P-channel FETs.

Figure 10:
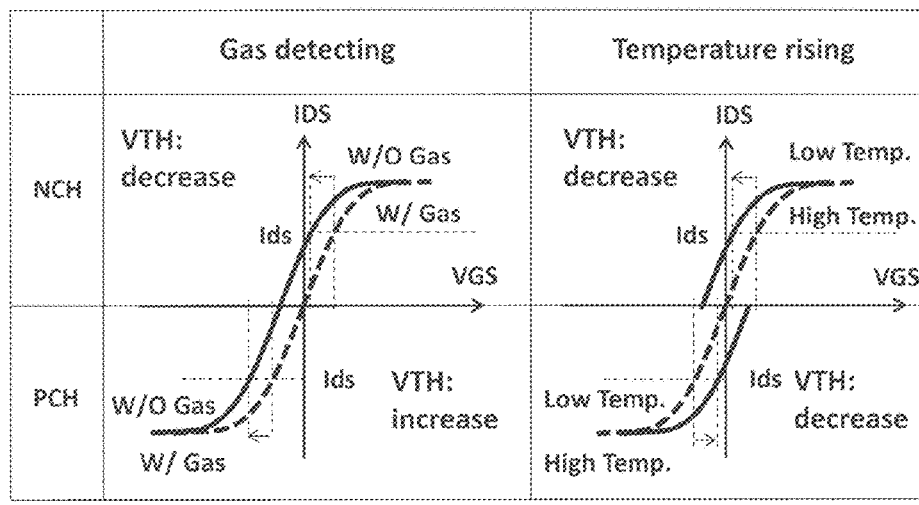
FIG. 10 A graphical representation showing a comparison of output characteristics between an N-channel FET-type hydrogen sensor and a P-channel FET-type hydrogen sensor.

Next, features specific to a P-channel FET will be described using FIG. 10. FIG. 10 shows a comparison of behavior when a detection target gas is sensed (Gas detecting) and behavior when the ambient temperature rises (Temperature rising) between a P-channel FET (PCH) and an N-channel FET (NCH). As the temperature range, it is assumed that the temperature is raised or lowered within, for example, the range in which the device is operable.

First, the behavior of the sensor FET when the detection target gas is sensed will be described. The dotted lines in the drawing show IDS-VGS characteristics when the gas is not present, and the solid lines show IDS-VGS characteristics when the gas is present. A threshold voltage VTH decreases in a detection target gas atmosphere in the N-channel sensor FET, and conversely increases in the P-channel sensor FET. However, the decrease in VTH in the P-channel sensor FET means that a gate-source voltage VGS required for obtaining the same drain current IDS decreases.

On the other hand, when the ambient temperature rises, VTH decreases, compared to that before temperature rise, in the N-channel FET, and VTH decreases also in the P-channel FET. The dotted line shows the IDS-VGS characteristics before temperature rise, and the solid line shows the IDS-VGS characteristics after temperature rise.

The directions of changes in VTH at the time of detection of the detection target gas and at the time of temperature rise are the same in the N-channel sensor FET, while the directions are opposite in the P-channel sensor FET. When the detection target gas is generated with temperature rise, the direction of output is opposite in the P-channel sensor FET; therefore, a VTH change due to the detection of the detection target gas and a VTH change due to temperature rise can be distinctly separated. On the other hand, the VTH changes cannot be separated in the N-channel sensor FET. In applications in which the generation of a detection target gas is accompanied by temperature rise, such as a FCV or a nuclear power plant, the P-channel sensor FET is advantageous over the N-channel in the sense that the possibility of erroneous detection can be reduced. Conversely, it can be said that when the generation of the detection target gas is accompanied by temperature drop, the N-channel sensor FET is more suitable than the P-channel.

The above described is the advantageous effect obtained by configuring the sensor FET and the reference FET using P-channel FETs.

Figure 11:
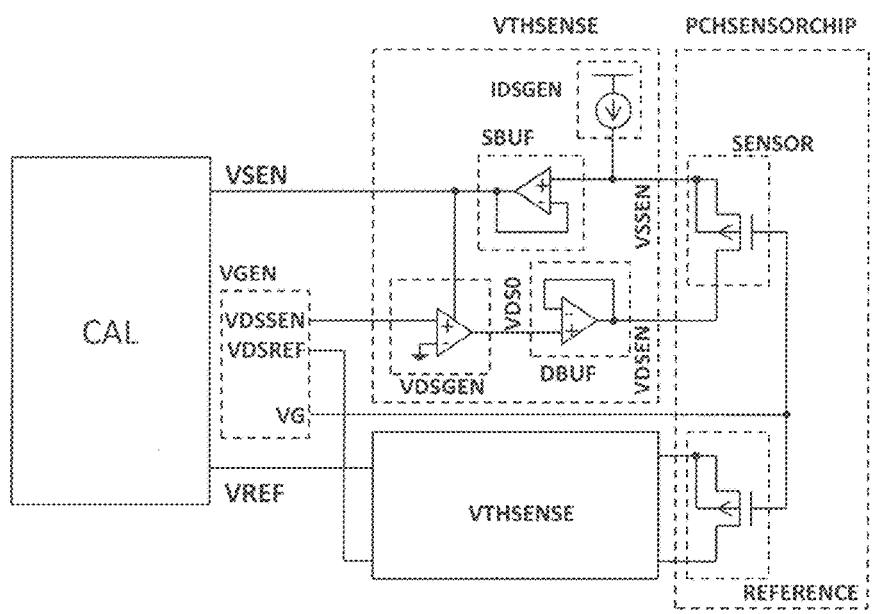
FIG. 11 A block diagram of a second example of a P-channel FET-type hydrogen sensor chip.

FIG. 11 describes one example of a specific configuration of the VTH detection circuit (VTHSENSE) in the sensor system (SENSORSYSTEM) shown in FIG. 6. The output of a drain-source current generating circuit (IDSGEN) that generates a constant drain current is connected to a source potential (VSSEN) for a sensor FET (SENSOR). A source voltage buffer (SBUF) receives the source potential (VSSEN) as an input and outputs the same voltage as the input to a sensor FET device output (VSEN). Due to this, even if the load of the sensor FET device output (VSEN) is large, the voltage level of the source potential (VSSEN) can be transmitted to the operation circuit (CAL).

A drain-source voltage generating circuit (VDSGEN) receives, as inputs, a drain-source voltage (VDSSEN) for sensor FET generated by the voltage generating circuit (VGEN) and the sensor FET device output (VSEN), and outputs (VDS0). The voltage (VDS0) has a magnitude obtained by adding together the difference voltage between the drain-source voltage (VDSSEN) for sensor FET and the ground based on the sensor FET device output (VSEN), and the sensor FET device output (VSEN). That is, VDS0=VSEN+VDSSEN.

Since the sensor FET device output (VSEN) is equal to the source potential of the sensor FET, the source-drain voltage of the sensor FET is maintained by the drain-source voltage generating circuit (VDSGEN) at the constant drain-source voltage (VDSSEN) for sensor FET. A drain voltage buffer (DBUF) outputs the voltage (VDS0) to a drain potential (VDSEN) for sensor FET. Due to this, there is the advantage that driving is possible even when a large load is connected to the drain potential (VDSEN) for sensor FET. Even in the situation where the VTH detection circuit (VTHSENSE) and a P-type FET sensor chip (PCHSEN-SORCHIP) are connected through a long cable, the drain-source voltage of the sensor FET is maintained at (VDS0) by the drain voltage buffer (DBUF). The VTH detection circuit (VTHSENSE) on the reference FET (REFERENCE) is also basically similar to that on the sensor FET side. It is sufficient that the operational amplifier in FIG. 11 is a commercially available operational amplifier having general characteristics.

A second example will be described below.

Figure 12:
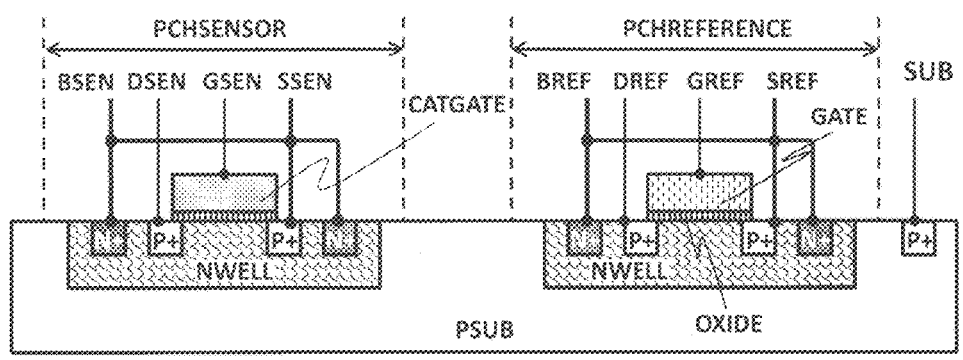
FIG. 12 A cross-sectional view of a first example of a P-channel FET-type hydrogen sensor system.

FIG. 12 shows the second example of a sensor chip. The second example is the same as the first example shown in FIG. 5 in that the P-channel sensor FET and the P-channel reference FET are formed on the P-type substrate (PSUB); however, the second example is different in that the gate of the reference FET is configured of a gate (GATE) that does not have a catalytic action on a detection target. In the configuration, a failure in which the reference FET has sensitivity to the detection target due to the degradation of the blocking film (PASSI) shown in FIG. 5 can be essentially avoided. However, the film formations of the gate (GATE) not having the catalytic action and the catalytic gate electrode (CATGATE) need to be separately performed, so that film forming process costs and the number of masks increase.

Figure 13:
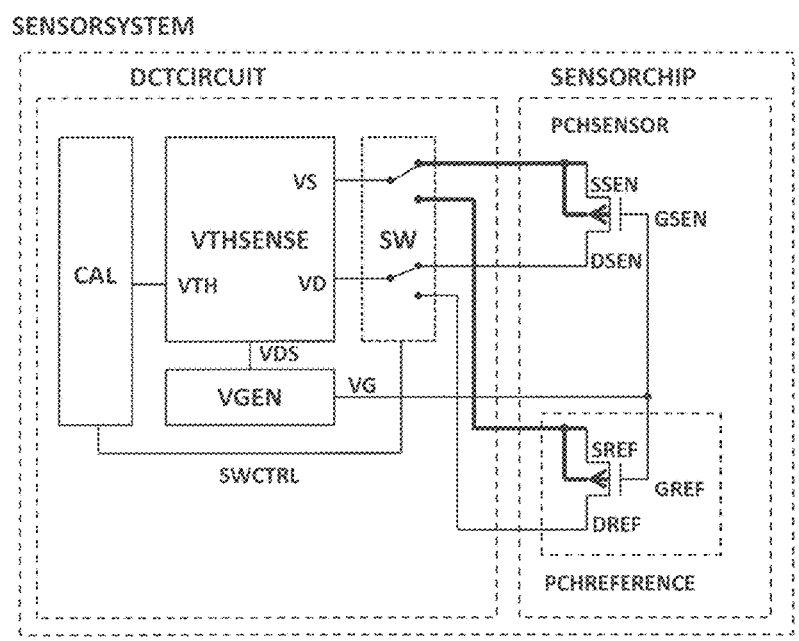
FIG. 13 A block diagram of a second example of a P-channel FET-type hydrogen sensor system.

FIG. 13 shows a second example of a sensor system. Compared to the first example shown in FIG. 6, the second example is different in that the number of the VTH sensing circuits (VTHSENSE) is reduced to one and that one VTH sensing circuit (VTHSENSE) is shared by the sensor FET and the reference FET through a switch SW. A switch control signal (SWCTRL) is generated by the correction operation circuit (CAL). By employing the configuration, compared to the case in which the VTH sensing circuits (VTHSENSE) are individually provided in the sensor FET and the reference FET, errors caused by a circuit variation can be reduced, and further, costs are reduced because the circuit configuration is simple. Since the sensor FET output and the reference signal output are alternately switched in a time-division manner, the simultaneity of measurement is lost. However, this disadvantage is eliminated by performing switching sufficiently faster than a gas concentration change time constant. Specifically, measurement accuracy is not affected if the switching is performed at a rate of 1 Hz or more.

Figure 14:
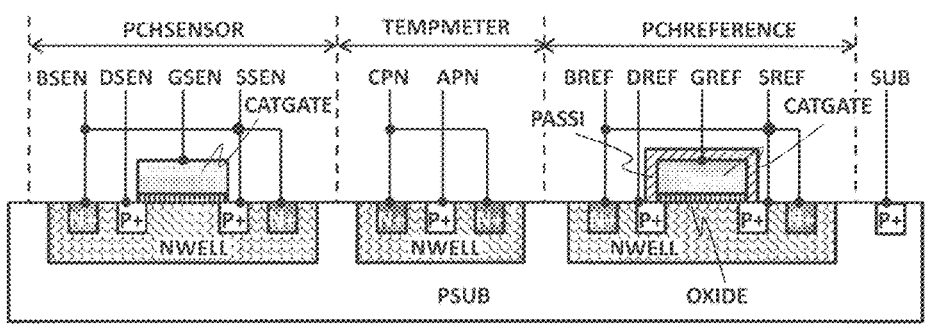
FIG. 14 A cross-sectional view of a first example in which a temperature meter using a PN junction is mounted.

FIG. 14 shows a third example of a sensor chip. The third example has a configuration in which a PN junction temperature meter (TEMPMETER) is added to the first example shown in FIG. 5. The PN junction is formed on the P-type substrate (PSUB), which is the same as that of the P-channel sensor FET and the P-channel reference FET. An anode terminal (APN) is connected to a P-diffusion region (P+), and a cathode terminal (CPN) is connected to an N-diffusion region (N+). The respective wells (NWELL) of the sensor FET, the reference FET, and the PN junction are electrically isolated from each other by setting the substrate potential (SUB) to the ground potential.

Although the gate of the reference FET in FIG. 14 is the catalytic gate electrode (CATGATE), the gate may be the gate (GATE) not having a catalytic action as shown in FIG. 12. That is, providing the PN junction temperature meter on the sensor chip and the configuration of the reference FET have no relation to each other.

Figure 15:
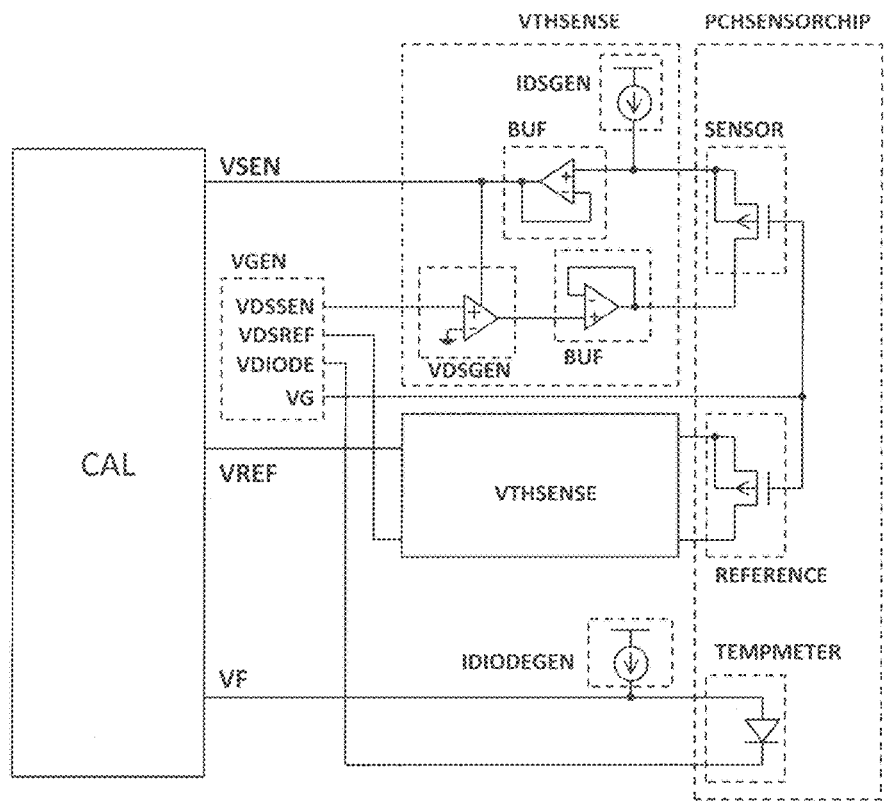
FIG. 15 A block diagram of one example of a hydrogen sensor system using a sensor chip of FIG. 13.

FIG. 15 shows a third sensor system example including the sensor chip of FIG. 14. Compared to FIG. 6, the example is different in that the temperature meter (TEMPMETER) configured of the PN junction is included on the sensor chip and that a circuit block that controls this temperature meter (TEMPMETER) is added.

A current to be supplied to the temperature meter (TEMPMETER) is generated in a current source (IDIODEGEN). A voltage (VDIODE) for properly controlling the temperature meter (TEMPMETER) is generated in the reference voltage generating circuit (VGEN). The temperature of the sensor chip is obtained by the operation circuit (CAL) using an anode potential (VF) of the temperature meter (TEMPMETER). In the operation circuit (CAL), control for keeping the chip temperature constant or a sensitivity correction operation of the sensor output is carried out using obtained chip temperature information. Since a FET-type gas sensor obtains an output due to a detection target gas being occluded by a catalytic metal, sensitivity changes due to the chip temperature. Therefore, it is desirable to provide the temperature meter on the chip and perform a sensitivity correction, for ensuring reliability in applications in which the ambient temperature changes.

Figure 16:
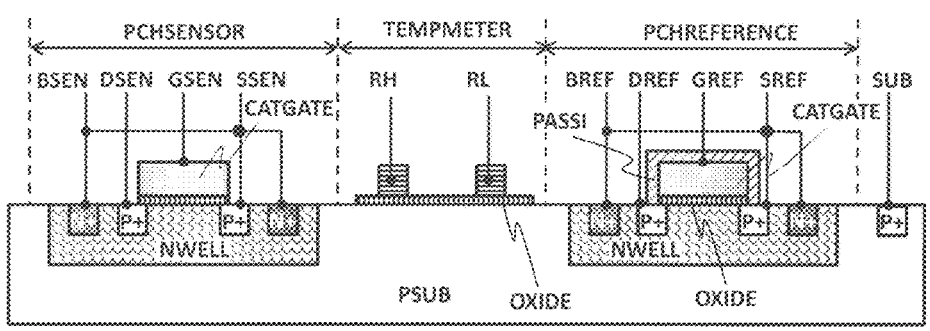
FIG. 16 A cross-sectional view of a first example in which a temperature meter using a metal interconnection resistance is mounted.

FIG. 16 shows a fourth example of a sensor chip. Compared to the third example shown in FIG. 14, the temperature meter (TEMPMETER) is configured using an interconnection resistance. FIG. 16 shows a certain cross-section of the entire interconnection resistance, and actually, it is assumed that the interconnection with a required length is formed on the chip. One end of the interconnection is extracted as an RH terminal (RH), and the other end is extracted as an RL terminal (RL). Since a metal interconnection resistance is a function of temperature, information of the chip temperature can be obtained by measuring the resistance value. The interconnection temperature meter can also be utilized as an electrothermal heater that adjusts the chip temperature. In this case, the RH terminal (RH) and the RL terminal (RL) also serve as a connection terminal and a resistance measurement terminal of a heater power source. There is also a method in which the RH terminal (RH) is separately prepared, such as RH1 and RH2, and the RL terminal (RL) is separately prepared, such as RL1 and RL2, because 4-terminal measurement is desirable for measuring the resistance value with good accuracy. As described in the description of FIG. 14, the gate of the reference FET may be replaced by the non-catalytic gate (GATE), and the sensing target blocking film (PASSI) may be removed. That is, the case in which the interconnection resistance temperature meter is applied to the second example of the sensor chip shown in FIG. 12 is also included in the scope of the present application.

Figure 17:
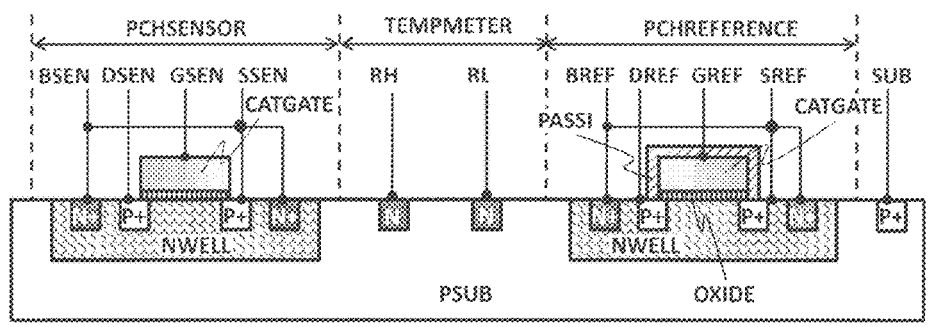
FIG. 17 A cross-sectional view of a first example in which a temperature meter using a diffusion layer resistance is mounted.

FIG. 17 shows a fifth example of a sensor chip. Compared to the fourth example shown in FIG. 16, the fifth example is different in that the resistance temperature meter (TEMP-METER) is formed of a diffusion layer resistance. Compared to the interconnection resistance temperature meter, the diffusion layer resistance temperature meter has the advantage of high stability. Moreover, since it is easy to achieve a higher resistance, the diffusion layer resistance temperature meter conceivably has advantages such as being capable of increasing heat generating efficiency when utilized as an electrothermal heater. Moreover, because of a configuration in which the interconnection is buried in the P-type substrate (PSUB), thermal efficiency when the diffusion layer resistance temperature meter is utilized as a heater can be improved compared to the interconnection resistance temperature meter. When the diffusion layer resistance temperature meter is utilized as an electrothermal heater, the RH terminal (RH) and the RL terminal (RL) also serve as a connection terminal and a resistance measurement terminal of a heater power source. There is also a method in which the RH terminal (RH) is separately prepared, such as RH1 and RH2, and the RL terminal (RL) is separately prepared, such as RL1 and RL2, because 4-terminal measurement is desirable for measuring the resistance value with good accuracy. Since the diffusion layer resistance temperature meter can be made simultaneously in the diffusion layer manufacturing step, the diffusion layer resistance temperature meter is preferable in that an increase in process costs can be suppressed. As described in the description of FIG. 14, the gate of the reference FET may be replaced by the non-catalytic gate (GATE), and the sensing target blocking film (PASSI) may be removed. That is, the case in which the interconnection resistance temperature meter is applied to the second example of the sensor chip shown in FIG. 12 is also included in the scope of the present application.

Figure 18:
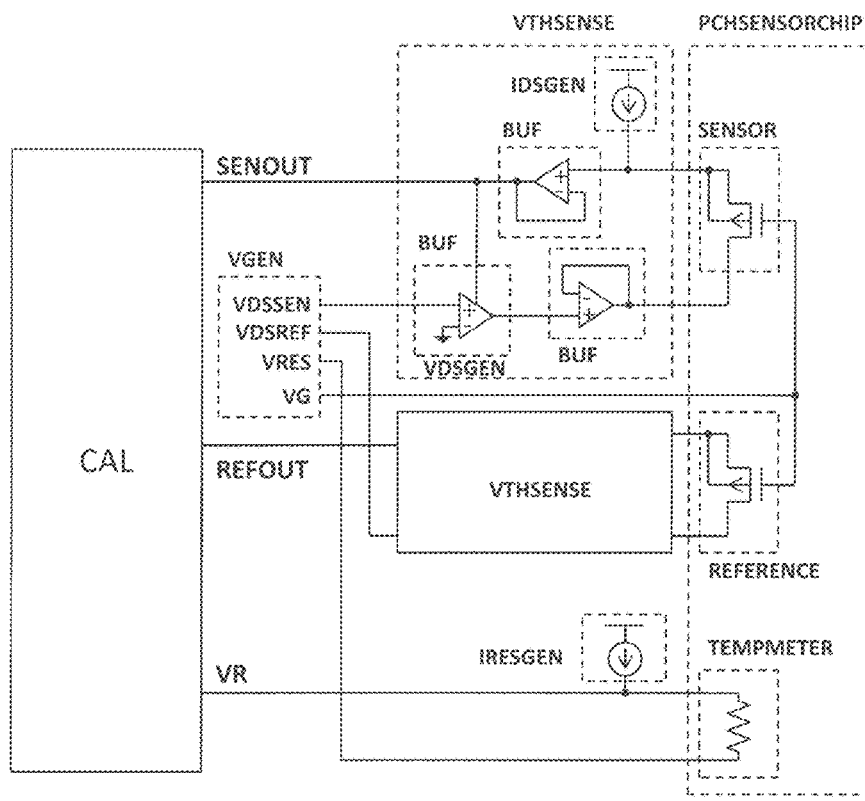
FIG. 18 A block diagram of one example of a hydrogen sensor system using a sensor chip of FIGS. 15 and 16.

FIG. 18 shows a fourth sensor system example of a sensor system using the sensor chip shown in FIGS. 16 and 17. Compared to FIG. 15, the example is different in that the temperature meter (TEMPMETER) is configured of a resistance. A current source (IRESGEN) is a circuit block that generates a current for controlling the temperature meter (TEMPMETER). A voltage (VRES) for controlling the resistance temperature meter is generated in the reference voltage generating circuit (VGEN). A resistance temperature meter output (VR) is input to the operation circuit (CAL). As described in the description of FIG. 15, higher reliability and higher stability can be achieved by performing the control of the chip temperature and a correction operation of the sensor output using the resistance temperature meter output (VR) including the chip temperature information.

Figure 19:
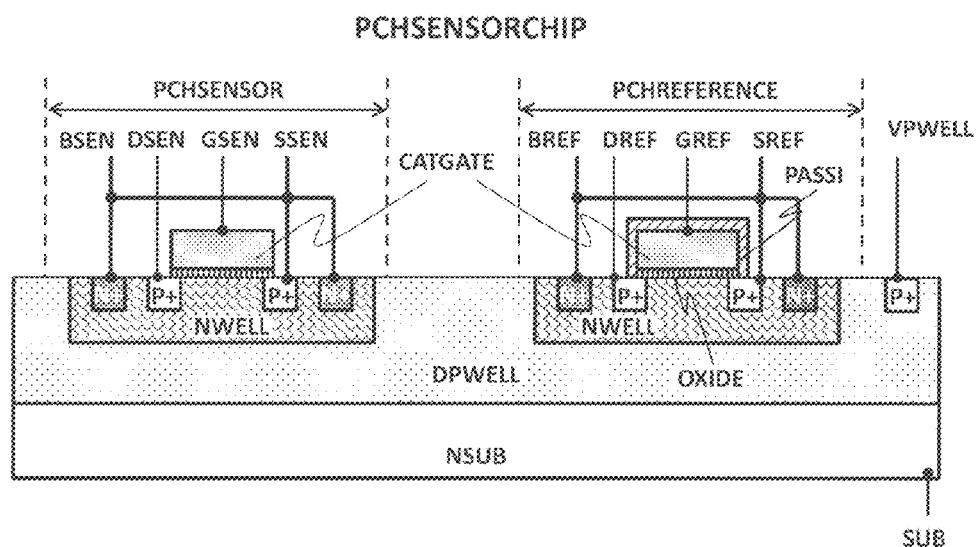
FIG. 19 A cross-sectional view of a third example of a P-channel FET-type hydrogen sensor chip.

FIG. 19 shows a sixth example of a sensor chip. In the case of using an N-type substrate (NSUB), a deep P-well (DPWELL) is provided on the N-type substrate (NSUB), and further, a P-channel sensor FET and a P-channel reference FET are formed on the deep P-well (DPWELL). Although process costs to constitute the deep P-well (DPWELL) increase, the sixth example is useful in applications in which the N-type substrate (NSUB) has to be used. In this case, it should be noted that the substrate potential (SUB) needs to be set, not to the ground, but to a high potential.

Figure 20:
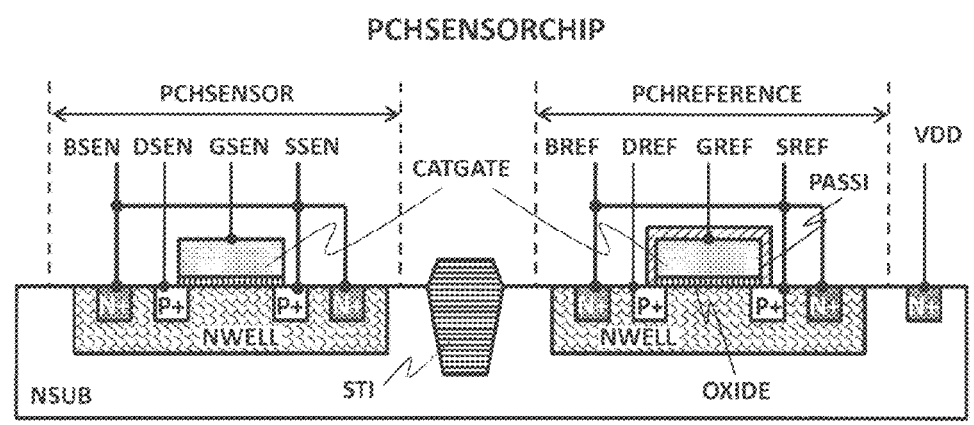
FIG. 20 A cross-sectional view of a fourth example of a P-channel FET-type hydrogen sensor chip.

FIG. 20 shows a seventh example of a sensor chip, in which the P-channel sensor FET and the P-channel reference FET are configured on the N-type substrate (NSUB) without the deep wells. For isolating the well potential of the sensor FET and the well potential of the reference FET from each other, a trench-type device isolation (STI) is provided therebetween. Due to this, since the impedance between the well of the sensor FET and the well of the reference FET increases, the well potentials can be controlled independently of each other; as a result, a configuration in which the substrate effect is eliminated by short-circuiting the well and the source can be realized.

Although not specified in FIGS. 19 and 20, the case in which the reference FET includes the non-catalytic gate (GATE) as shown in FIG. 12, the case in which the PN junction temperature meter (TEMPMETER) shown in FIG. 14 is included, the case in which the interconnection resistance temperature meter (TEMPMETER) shown in FIG. 16 is included, and the case in which the diffusion layer resistance (TEMPMETER) shown in FIG. 17 is included are also included as similar derivative examples in the scope of the present application.

Although the effect of reducing the 1/f noise cannot be expected, the configuration in which the substrate effect is eliminated by short-circuiting the well and the source can be realized also in the case of using an N-channel FET.

Figure 21:
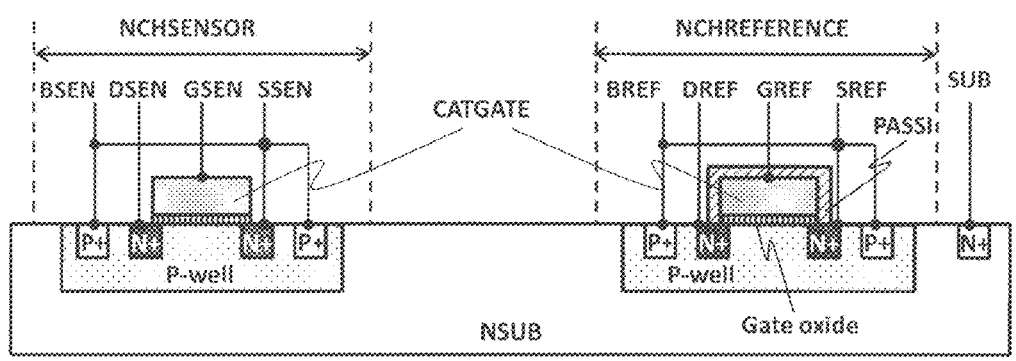
FIG. 21 A cross-sectional view of a first example of an N-channel FET-type hydrogen sensor chip.

FIG. 21 shows an eighth example in which, with respect to the first example shown in FIG. 5, the P-type substrate is replaced by the N-type substrate (NSUB) and the P-channel FET is replaced by an N-channel FET.

Figure 22:
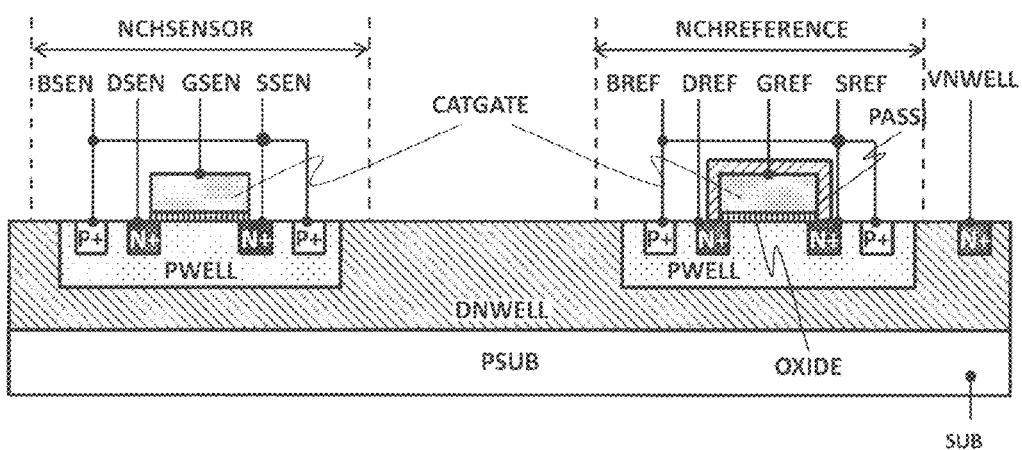
FIG. 22 A cross-sectional view of a second example of an N-channel FET-type hydrogen sensor chip.

FIG. 22 shows a ninth example in which, with respect to the sixth example shown in FIG. 19, the N-type substrate is replaced by the P-type substrate (PSUB), the deep P-well is replaced by the deep N-well (DNWELL), and the P-channel FET is replaced by an N-channel FET.

Figure 23:
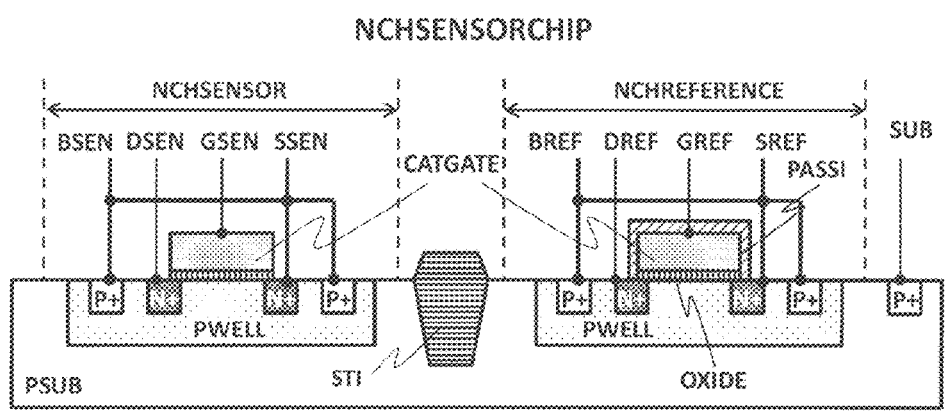
FIG. 23 A cross-sectional view of a third example of an N-channel FET-type hydrogen sensor chip.

FIG. 23 shows a tenth example in which, with respect to the seventh example shown in FIG. 20, the N-type substrate is replaced by the P-type substrate (PSUB) and the P-channel FET is replaced by an N-channel FET.

FIG. 24 each show one example of a cross-sectional structural drawing when a semiconductor device is configured of the P-channel FET shown in FIG. 5. The N-well (NWELL) is formed on the P-type substrate (PSUB), and the P-type FET is formed in the N-well (NWELL). Both the sensor FET (PCHSENSOR) and the reference FET (PCHREFERENCE) include a catalytic gate electrode (SCATGATE, RCATGATE); however, the catalytic gate electrode (SCATGATE) of the sensor FET is exposed in a through hole formed in the blocking film (PASSI), whereas the catalytic gate electrode (RCATGATE) of the reference FET is covered by the blocking film (PASSI). Under the catalytic gate electrode, a gate oxide film (OXIDE) is present. Moreover, there are a device isolation film (OX1) and an interlayer film (OX2).

The drain terminal (DREF) of the reference FET is connected to a drain pad (DRAINPAD), the source terminal (SREF) of the reference FET is connected to a source pad (SREFPAD), the well terminal (BREF) of the reference FET is connected to a body pad (BREFPAD), the catalytic gate electrode (RCATGATE) is connected to a gate pad (RCATGATEPAD), a substrate (SUB) is connected to a substrate potential pad (SUBPAD), and thus, signals can be input or output.

The drain terminal (DSEN) of the sense FET is connected to a drain pad (DRAINPAD), the source terminal (SSEN) of the reference FET is connected to a source pad (SSENPAD), the well terminal (BSEN) of the reference FET is connected to a bodypad (BSENPAD), the catalytic gate electrode (SCATGATE) is connected to a gate pad (SCATGATEPAD), and thus, signals can be input or output.

Figure 24A:
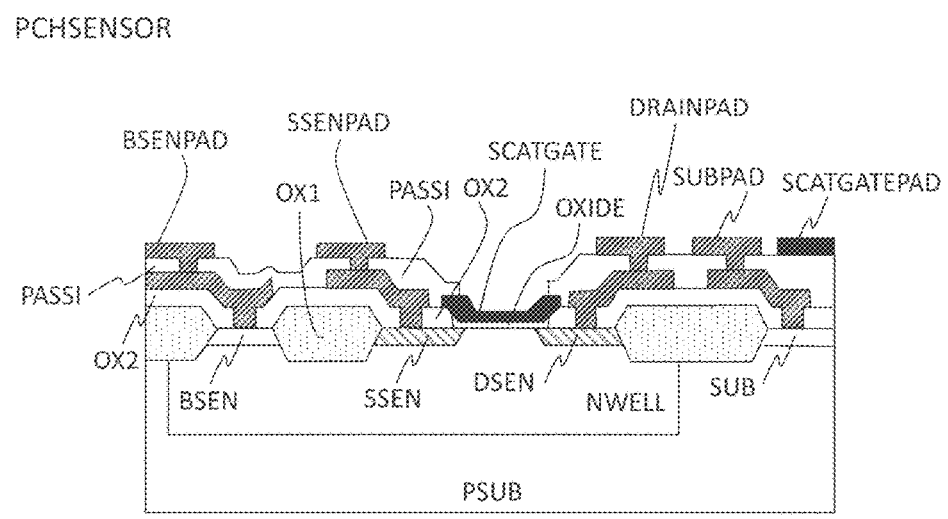
FIG. 24A A cross-sectional view of a sensor chip, including an interconnection layer and a protective layer.
Figure 24B:
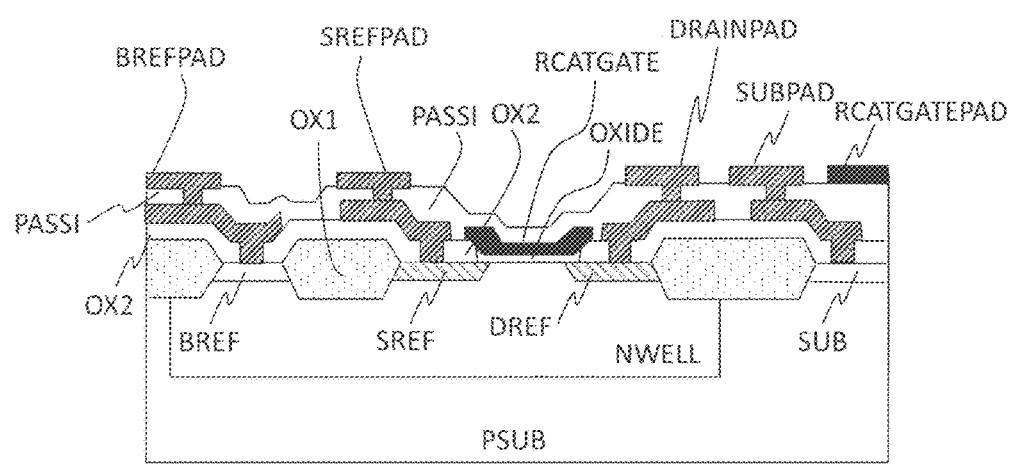
FIG. 24B A cross-sectional view of a reference chip, including an interconnection layer and a protective layer.

The sensor FET (PCHSENSOR) and the reference FET (PCHREFERENCE) are separately shown in FIGS. 24A and 24B for the purpose of comparative description; actually, however, the sensor FET (PCHSENSOR) and the reference FET (PCHREFERENCE) are formed on the common P-type substrate (PSUB).

Although not specified also in the eighth to tenth examples, the pattern in which the gate of the reference FET is configured of the non-catalytic gate (GATE), the case in which the PN junction temperature meter (TEMPMETER) shown in FIG. 14 is included, the case in which the interconnection resistance temperature meter (TEMPMETER) shown in FIG. 16 is included, and the case in which the diffusion layer resistance (TEMPMETER) shown in FIG. 17 is included are also included as similar derivative examples in the scope of the present application. That is, the invention is not limited to the embodiments described above but includes various modified examples. For example, a portion of the configuration of a certain example can be replaced by the configuration of another example, and moreover, the configuration of a certain example can be added to the configuration of another example. Moreover, as to a portion of the configuration of each example, the addition, removal, or replacement of the configuration of another example is possible.

The functions of the "source" and "drain" of a transistor may be interchanged when a transistor having a different polarity is employed or when the direction of a current changes in circuit operation. For this reason, in the description, the terms "source" and "drain" can be interchanged and used in some cases.

The terms "electrode" and "interconnection" in the description and the like do not functionally limit these components. For example, the "electrode" may be used as a portion of the "interconnection", and vice versa. Further, the terms "electrode" and "interconnection" include the case in which a plurality of "electrodes" or "interconnections" are integrally formed.

INDUSTRIAL APPLICABILITY

The FET-type sensor of the invention is a technique that can also be applied to a hydrogen concentration meter in a hydrogen infrastructure such as a fuel cell vehicle or a hydrogen station, as well as in various types of plants or a nuclear power plant.

REFERENCE SIGNS LIST

FET field-effect transistor
FCV fuel cell vehicle
VDS drain-source voltage
VG gate potential based on ground potential
VREF reference FET device output
PASSI detection target blocking film
OXIDE gate oxide film
CATGATE catalytic metal gate
DREF drain terminal of reference FET
SREF source terminal of reference FET
BREF well terminal of reference FET
IDS drain-source current
WELL well
SUB semiconductor substrate
PSUB P-type semiconductor substrate
VSEN sensor FET device output
DIPOLE hydrogen dipole
DSEN drain terminal of sensor FET
SSEN source terminal of sensor FET
BSEN well terminal of sensor FET
DCTCIRCUIT detection circuit
VTHSENSE VTH detection circuit
VDSEN drain potential for sensor FET
VSSEN source potential for sensor FET
VDSSEN drain-source voltage for sensor FET
VGEN reference voltage generating circuit
VDSREF drain-source voltage for reference FET
VDREF drain potential for reference FET
VSREF source potential for reference FET
CAL correction operation circuit
VDD High-side power source potential
VBS substrate voltage
VGS gate-source voltage
VTH threshold voltage
GATE non-catalytic gate
IDSGEN drain-source current generating circuit
SBUF source voltage buffer
DBUF drain voltage buffer
VDSGEN drain-source voltage generating circuit
SW changeover switch
SWCTRL changeover-switch control line
APN anode terminal of PN junction
CPN cathode terminal of PN junction
TEMPMETER temperature meter
VDIODE control voltage for PN junction
IDIODEGEN control current generating circuit for PN junction
VF PN junction temperature meter output
RH HIGH terminal for resistance temperature meter
RL LOW terminal for resistance temperature meter
VRES control voltage for resistance temperature meter
IRESGEN control current generating circuit for resistance temperature meter
DPWELL deep P-well
DNWELL deep N-well
STI trench-type device isolation

The invention claimed is:

1. A hydrogen sensor system comprising:
a P-type semiconductor substrate;
a sensor FET that is formed of a P-type FET within a first N-well formed on the P-type semiconductor substrate;
a reference FET that is formed of a P-type FET within a second N-well formed on the P-type semiconductor substrate; and
a detection circuit that detects a difference between threshold voltages of the sensor FET and the reference FET in a gas atmosphere, wherein:
the sensor FET and the reference FET are formed adjacent to each other, and having same structured P-type FET,
the sensor FET has sensitivity to hydrogen and the reference FET is covered by a blocking film which does not have hydrogen permeability, so as the reference FET does not have sensitivity to hydrogen,
the first N-well and second N-well are formed independently, the P-type semiconductor substrate is ground potential and the first N-well and the second N-well are electrically isolated from each other, and potential of first N-well and potential of second N-well are controlled independently, and
a source terminal of the sensor FET and a well terminal of the first N-well are short-circuited, and a source terminal of the reference FET and a well terminal of the second N-well are short-circuited.

2. The hydrogen sensor system according to claim 1, further comprising:
a first source-follower circuit that measures the threshold voltage of the sensor FET; and a second source-follower circuit that measures the threshold voltage of the reference FET and is provided independently of the first source-follower circuit.

3. The hydrogen sensor system according to claim 1, further comprising a source-follower circuit that measures the threshold voltage of the sensor FET and the threshold voltage of the reference FET, wherein in measuring the threshold voltage of the sensor FET and the threshold voltage of the reference FET, the source-follower circuit and the sensor FET or the source-follower circuit and the reference FET are switched and connected through switching.

4. The hydrogen sensor system according to claim 1, further comprising a PN junction portion for temperature measurement on the P-type semiconductor substrate.

5. The hydrogen sensor system according to claim 1, wherein:
   the sensor FET includes a first catalytic gate electrode and the first catalytic gate electrode is covered by a film having a through hole; and
   the reference FET includes a second catalytic gate electrode and the second catalytic gate electrode is covered by the blocking film which does not have hydrogen permeability.

6. The hydrogen sensor system according to claim 1, further comprising:
   a drain current source for sensor FET that is connected to the short-circuited well terminal of the first N-well and the source terminal of the sensor FET;
   a source voltage buffer for sensor FET that receives source potential of the sensor FET as an input and outputs the input to the detection circuit;
   a source-drain voltage generating circuit for sensor FET that maintains a source-drain voltage of a sensor FET constant;
   a drain current source for reference FET that is connected to the short-circuited well terminal of the second N-well and the source terminal of the reference FET;
   a source voltage buffer for reference FET that receives the source potential of the reference FET as an input and outputs the input to the detection circuit; and
   a source-drain voltage generating circuit for reference FET that maintains a source-drain voltage of a reference FET constant.

7. The hydrogen sensor system according to claim 1, wherein a structure that generates a signal corresponding to temperature is provided on the semiconductor substrate.

8. The hydrogen sensor system according to claim 7, wherein a PN junction is provided as the structure generating the signal corresponding to temperature.

9. The hydrogen sensor system according to claim 7, wherein a resistance member is provided as the structure generating the signal corresponding to temperature.

10. The hydrogen sensor system according to claim 1, wherein a sensor signal output terminal that outputs a signal representing a threshold voltage of the sensor FET or a change in the threshold voltage;
   a reference signal output terminal that outputs a signal representing a threshold voltage of the reference FET or a change in the threshold voltage;
   a source potential of the source terminal of the sensor FET, which is short-circuited with the well terminal of the first N-well, is output to the sensor signal output terminal, and
   a source potential of the source terminal of the reference FET, which is short-circuited with the well terminal of the second N-well, is output to the reference signal output terminal.

* * * * *